United States Patent [19]

Alexander

[11] Patent Number: 5,612,060
[45] Date of Patent: Mar. 18, 1997

[54] ENHANCEMENT OF TRANSPLANT GRAFT SURVIVAL THROUGH NUTRITIONAL IMMUNOMODULATION AND IMMUNOSUPPRESSIVE THERAPY

[76] Inventor: J. Wesley Alexander, 2869 Grandin Rd., Cincinnati, Ohio 54208

[21] Appl. No.: 452,550

[22] Filed: May 25, 1995

[51] Int. Cl.⁶ .................. A61K 35/14; A61K 31/505; A61K 31/52; A61K 31/195; A61K 31/20; A61K 31/395
[52] U.S. Cl. .................. 424/529; 514/45; 514/46; 514/47; 514/48; 514/49; 514/50; 514/51; 514/565; 514/564; 514/560; 514/183
[58] Field of Search ............... 424/529; 514/45, 514/46, 47, 48, 49, 50, 51, 565, 564, 560, 183

[56] References Cited

U.S. PATENT DOCUMENTS 5,231,085   7/1993   Alexander et al. .................. 514/44

OTHER PUBLICATIONS

Miller, C., et al., Prolongation of Rat cardiac Allografts by Pretransplant Administration of Blood Transfusions and Cyclosorin A, 1982; vol. 33; pp. 335–337.

Levy A., et al., The Significance of Timing of Additional Short–Term immunosuppression in the Donor–Specific Transfusion/Cyclosorine–Treated Rat; vol. 62, 1–000, No. 2, Jul. 27, 1996.

Chandra R. et al., Effect of Two Feeding Formulas on Immune Responses and Mortality in Mice Challenged with Listeria Monocytogenes; 1991; vol 27; pp. 45–48.

Kulkarni, A., et al., Influence of Dietary Glutamine and IMPACT® on In Vivo Cell–Mediated Immune Respnse in Mice; Nutrition 1990; vol. 6; pp. 66–69.

Lieberman., et al., Effect of Nutrient Substrates on Immune Function, Nutrition 1990; vol. 6; pp. 88–91.

Van Buren, C. et al., The Role of Nucleotides in Adult Nutrition; American institute of Nutrition; vol. 124; pp. 160S–164S, 1994.

Barbul, Adrian, Arginine and Immune Function; Nutrition; vol. 6, No. 1, Jan./Feb. 1990,pp. 53–58.

Katz, D., et al., Entral nutrition: Potential Role in Regulating Immune Function; Current Opinion in Gastroenterology; 1990, vol. 6; pp. 199–203.

Daly, J., et al., Enteral Nutrition with Supplemental Arginine, RNA and Omega–3 Fatty Acids in Patients After Operation: Immunologic, Metabolic and Clinical Outcome; Surgery 1992, vol. 112, pp. 56–67 .

Gottschlich M., et al., Differential Effects of Three Enteral Dietary Regimens on Selected Variables in Burn patients; JPEN 1990; vol. 14; pp. 225–236.

Alexander, J. Wesley, et al., Nutritional Immunomodulation in Burn Patients; Crit. Care Medicine; 1990; vol. 18; pp. S149–S153.

Bower, R., et al., Early Enteral Administration of a Formula (IMPACT®) Supplemented with Argine, Nucleotides, and Fish Oil in Intensive Care Unit Patients: Resulyts of a Multicenter, Prospective, Randomized Clinical Trial; Critical Care Med. 1995; vol. 23(3); pp. 436–449.

Ono K., et al., Improved Technique of Heart Transplantation in Rats; J. Thoracic Cardiovascular Surgery 1969; vol. 55; pp. 1107–1112.

Daly, John M., et al., Effect of Dietary Protein and Amino Acids on Immune Function; Critical Care Medicine; 1990; vol. 18; pp. S86–S93.

Virella, G., et al., Immunosuppressive Effects of Fish oil in Normal Human Volunteers: Correlation with the In Vitro Effects of Eicosapentanoic Acid on Human Lymphocytes; Clinical Immunology and Immunopathology; 1991; vol. 61; pp. 161–176.

Kline K., et al., RRR–α–Tocopheryl Succinate Inhibition of Lectin–Induced T Cell Proliferation; Nutrition –Cancer; 1993; vol. 19; pp. 241–252.

Perez, R., et al., Dietary immunoregulation of Transfusion–induced Immunosuppression; Transplantation 1988; vol. 45; pp. 614–617.

Homan Van Der Heide, J., et al., Effect of Dietary Fish Oil on Renal Function and Rejection in Cyclosporine–Treated Recipients of Renal Transplants; New England Journal of Medicine; 1993; vol. 329; pp. 769–773.

Shimamura, T., et al., Influence of Dietary Fish Oil on the Aortic, Myocardial, and Renal lesions of SHR; J. Nutritional Sci. Vitaminology of Tokyo; 1991; vol. 37; pp. 581–590.

Homan van der Heide J., et al., The Effects of Dietary Fish Oil on Renal Function in Cyclosporine–treated Renal Transplant Recipients; Transplantation 1990; vol. 49; pp. 523–527.

Barbul, A., et al., Arginine: Thymotrophic and Wound Healing Promoting Agent; Surg. Forum 1977; vol. 28; p. 101.

Eagle H., Amino Acid Metabolish in Mammalian Cell Cultures; Science 1959; vol. 130; pp. 432–437.

Daly J., et al., Immune and Metabolic Effects of Arginine in the Surgical patient; Ann. Surg. 1988; vol. 208; pp. 512–522.

Seegmiller, J., Immunologic Aspects of Purine Metabolism; Adv. Exp. Med. Biol 1977; vol. 76; p. 412.

Goodnight, S., et al., The Effect of Dietary Omega–3 fatty acids on Platelet Composition and function in Man; Blood 1981; vol. 58; pp. 880–885.

Sarris, G., et al., Inhibition of Accelerated Cardian Graft Arteriosclerosis by Fish Oil; J. Cardiovascular Surg. 1989; vol. 97; pp. 841–855.

Kinsella, J., et al., Dietary Polyunsaturated Fatty Acids and Eicosanoids: Potential Effects on the Modulation of Inflammatory and Immune Cells: an Overview; Nutrition; 1990; vol. 6; pp. 24–44.

Primary Examiner—Marianne M. Cintins
Assistant Examiner—William R. A. Jarvis
Attorney, Agent, or Firm—Robert S. Honor; Carl W. Battle

[57] ABSTRACT

An improved immunomodulatory therapy for enhancement of depressed host defense mechanisms as shown by improved allograft survival rates is disclosed. The therapy comprises the synergistic combination of an immunomodulatory diet consisting of an amino acid such as arginine, ornithine and their salts, a nucleotide such as RNA and fish oil as a source of omega-3-fatty acids together with an immunosuppressive treatment comprising the administration of a donor specific transfusion and cyclosporine.

18 Claims, No Drawings

ENHANCEMENT OF TRANSPLANT GRAFT SURVIVAL THROUGH NUTRITIONAL IMMUNOMODULATION AND IMMUNOSUPPRESSIVE THERAPY

FIELD OF INVENTION

The present invention relates generally to therapeutic regimens for immunologically impaired individuals recovering from surgery, infection, burns and other trauma. More specifically, the invention relates to an immunomodulatory diet and immunosuppressive therapy for the enhancement of host defense mechanisms and prolongation of allograft survival.

BACKGROUND OF THE INVENTION

The physiological trauma that besets the human body as a result of surgery, cancer, intensive burns, radiation therapy and the like has a deleterious effect on the health of the individual in more ways than one. It is well known that patients recovering from such trauma and who are being therapeutically treated often have compromised host defense mechanisms. A damaged or reduced immune system can often lead to increased morbidity and eventual death as a result of infection and/or organ failure through rejection.

In a related case U.S. Pat. No. 5,231,085 also to Alexander et. al., the present applicants discovered novel immunomodulatory compositions and methods which enhance host defense mechanisms which have been compromised and are deficient for one reason or another. The immunomodulatory compositions are composed of an amino acid such arginine or ornithine that are used in the biosynthetic pathways of other polyamines, a nucleobase source and a combination of omega-3- and omega-6-polyunsaturated fatty acids. The composition is administered enterally or modified for parenteral administration and is preferably used as a supplement to a complete nutritional diet meeting the complete daily caloric and vitamin requirements of the patient. The administration of these compositions restore damaged or compromised immune systems to their healthy state. The Alexander et. al. '085 patent is hereby incorporated by reference.

The immunomodulatory compositions of Alexander et. al. '085 are believed to decrease the damage caused by the inflammatory response through multiple immune functional pathways. These compositions, when administered to surgery patients during the early post-operative period have been shown to bring about a significant reduction in the length of the average hospital stay as well as a significant reduction in the number of wound complications.

It is also well documented that the administration of lipids such as those found in a number of common fish oils significantly reduce the degree of immune response to solid organ allografts leading to improved survival. In one study, fish oil supplementation reduced the number of rejection episodes of renal allografts during the first year post-operative by 60%. Omega-3-polyunsaturated fatty acids which are found in these fish oils in fact have several properties which suggest that they play a key role in the inflammatory response. They are known to be potent inhibitors of platelet aggregation, thrombus formation and appear to reduce small vessel arteriosclerosis. These effects are presumed to occur through the down regulation of TxA-2 production in multiple cell lines.

Arginine and RNA precursors have also been associated with the enhancement of immune responses. Numerous studies have documented the significant role of arginine in immune system immunomodulation. Supplementing the diet with arginine has been noted to increase thymic weight as well as enhance T-cell responsive to mitogens. In in vitro models, arginine appears to be an absolute requirement for lymphocyte blastogenic response. Cancer patients undergoing major operative surgery who received enteral feedings supplemented with arginine experienced significant enhancement in T-cell activation to Con A and PHA stimulation. RNA precursors are also felt to be a rate-limiting metabolite in the propagation of immune cells and their supplementation has been associated with enhanced immune proliferation. Moreover, certain rapidly growing cells, such as T-lymphocytes appear to lack the ability to synthesize nucleotides and depend on salvage pathways to obtain sufficient amounts of nucleotides to continue growth.

SUMMARY OF THE INVENTION

The present invention comprises an improved immunomodulatory therapy comprising the synergistic combination of an immunomodulatory diet and an immunosuppressive treatment for the enhancement of allograft survival and altered host defense mechanisms. The immunomodulatory diet consists of a mixture of arginine and/or ornithine and their salts together with either RNA, nucleabase, nucleotides, DNA and mixtures thereof as well as omega-3-polyunsaturated fatty acids. The diet is fed as a fully nutritional formula together with a therapeutic dosage form of a donor specific transfusion and cyclosporine.

DETAILED DESCRIPTION OF THE INVENTION

Allograft survival rates are dependant upon a wide variety of factors and can be enhanced as noted previously herein. It is not expected however, that a synergistic increase in the graft survival rate could result from their treatment with an enteral immunomodulatory diet and an immunosuppressive treatment comprising the administration of a donor specific transfusion and cyclosporine.

The immunomodulatory compositions of the present invention consist generally of:

a) A compound associated with the synthesis of polyamines, b) A nucleobase source, and c) Omega-3-polyunsaturated fatty acids.

The term "a compound associated with the synthesis of polyamines" as used herein is intended to include, but not limited to arginine, arginine precursors, ornithine and the like, in free amino acid form or salt form. The composition relates in particular to arginine. Though part of the ornithine and arginine may be administered in protein form, the arginine and ornithine content of proteins will in general be so low that the contribution of any added protein source to the arginine and ornithine content of the composition of the invention can be ignored.

The amount of arginine supplied may vary within wide ranges, depending on the desired treatment, the subject to be treated and his needs. Thus, where the subject to be treated is an adult person (typically of about 60 to 75 kg body weight) a satisfactory immunomodulatory response is, in general, obtained with compositions formulated to allow a daily administration of 3 to 40 grams, preferably 10 to 30 grams and most preferably 15 to 22 grams of arginine (in free amino acid form). Ornithine and/or other compounds associated with the synthesis of polyamines, may be substituted on a 1:1 molar ratio for arginine, or used in combination with arginine.

Nucleobase sources suitable for use in the composition of the invention comprise or consist of natural nucleobases, nucleosides, nucleotides, RNA, DNA equivalents thereof and/or mixtures comprising one or more of these compounds. Preferably RNA is used as it also appears to elicit the greatest immunomodulatory response.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythmidine and deoxycytidine.

Natural nucleotides include the phosphate esters of natural nucelosides such as monophosphate adenylate (AMP), guanylate (GMP), uridylate (UMP), cytidylate (CMP), deoxythymidylate (dTMP), deoxycytidylate (dCMP), and the diphosphates and triphosphates of natural nucleosides such as ADP and ATP.

A purified nucleobase source, such as yeast, is preferred. However, other sources such as meat and the like may be used.

The amount of nucleobase source to be administered will depend on the type of treatment desired, the subject to be treated and the like. Thus, again where the subject to be treated is an adult person, a satisfactory immunomodulatory response is, in general, obtained with compositions of the invention formulated to allow a daily administration of from about 0.1 to 4.0 grams, preferably about 1.0 to 3.0 grams and most preferably from about 1.25 to 2.5 grams of RNA, or an equivalent amount of another nucleobase source. For the purpose of this invention, one weight unit of nucleobase is regarded to be equivalent to 2.5 to 3.0 weight units of RNA, DNA, other nucleosides or nucleotides.

For this purpose of this invention the omega-3-polyunsaturated fatty acids (PUFA) may be in free acid form or in a form suitable for the physiological supply of omega-3-PUFAs, such as in triglyceride form. Examples of omega-3 PUFAs particularly appropriate for use in the compositions of the invention include eicosapentaenoic acid (EPA) and docosahexaenoic acid (DH). Suitable sources for such omega-3-PUFAs are well known and include linseed oil and fish oils such as menhaden oil, salmon oil, mackerel oil, tuna oil and anchovy oil, in particular menhaden oil.

The amount of omega-3-PUFAs to be administered will depend on the type of treatment, the subject to be treated and the like. Here again where the subject to be treated is an adult person, a satisfactory immunomodulatory response is, in general, obtained with compositions of the invention formulated to allow a daily supply of from about 0.1 to about 20.0 grams, preferably from about 0.1 to about 15.0 grams and most preferably from 0.15 to 10.0 grams of omega-3-polyunsaturated fatty acid.

The immunomodulatory diet composition aspect of the present invention will also preferably include vitamins, minerals, trace elements as well as additional nitrogen, carbohydrate and fatty acid sources. These would most preferably take the form of a liquid complete nutritional diet so that it can be used as the sole source of nutrition supplying essentially all the required daily amounts of vitamins, minerals, carbohydrates, fatty acids and the like.

Suitable nitrogen sources include proteins such as caseinates or protein hydrosylates. Suitable carbohydrate sources include various starches and maltodextrins while suitable fatty acid sources include the triglycerides. Preferably, the supplement should provide an energy supply of from about 750 to 3500 kcal/day and most preferably from about 1000 to about 2000 kcal/day.

The immunomodulatory compositions of the invention may be formulated in a manner suitable for parenteral or enteral administration. They are particularly appropriate for enteral use, such as oral administration and/or tube feeding. Such compositions are conveniently administered in the form of an aqueous liquid. The compositions of the invention suitable for enteral application are accordingly preferably in aqueous form or in powder form, whereby the powder is conveniently added to water prior to use. For use as tube feeding, the amount of water to be added will depend on the patients's fluid requirements and condition.

The immunomodulatory diet administered by itself exhibits improved results with respect to allograft survival rates. However, these rates are greatly increased when the diet is administered in conjunction with an immunosuppressive treatment comprising the additional administration of a dosage form consisting of a donor specific transfusion and cyclosporine.

Cyclosporine ($C_{62}H_{111}N_{11}O_{12}$) is a non-polar cyclic oligopeptide derived from the fungus *Tolypocladium inflatum* that exhibits immunosuppressive activity through the disablement of T-cells. The cyclosporine is administered to the patient together with the donor specific transfusion in a therapeutically effective amount of from about 5.0 mg/kg to about 15.0 mg/kg.

Donor specific transfusion is a known immunological procedure that has been used clinically for some time. Anticoagulated blood from the donor is either administered whole or is first fractionated into its cellular components using standard separation procedures such as centrifugation. The blood, either whole or fractionated is then injected into the transplant subject together with a dose of cyclosporine which is given orally or may be injected intravenously. The dosage of cyclosporine may vary considerably according to the patients body weight, metabolism, etc. but generally initial doses will range from about 5.0 to about 15.0 mg/kg per day. This will then change according to the patients response. Intravenous doses are generally one-third (⅓) that of the oral doses. Without being bound to any theory, it is believed that the immunological response to donor specific transfusion and cyclosporine is not merely a passive response but is generated by proliferation of suppressive elements leading to an active reduction of alloreactive cells.

The following examples are provided in order to better describe and set forth that which the Applicants' conceive their invention to be. It is recognized that minor variations or changes may be made with respect to the materials or procedures that are not disclosed herein. It is to be understood that to the extent any such changes do materially alter or modify the invention, they are deemed as falling within the spirit and the scope of the invention as recited by the claims that follow.

EXAMPLE 1

The following example shows the extent to which allograft survival was improved by the subsequent administration of an immunomodulatory diet together with the immunosuppressive therapy of the present invention in a Lewis rat cardiac transplant model.

Male ACI rats (Harlan Industries, Inc. Indianapolis, Ind.), weighing 250–300 grams served as donors of whole blood for transfusion and cardiac allografts. Male Lewis rats weighing 250–300 grams were the recipients. All animals used in the study were housed in individual steel cages under supervised conditions in a facility approved by the American Association for Accreditation of Laboratory Animal Care (AAALAC). Either standard rodent chow or the immunomodulatory diet and water were provided ad libitum. The immunomodulatory diet contained:

15.0 grams of arginine 2.0 grams RNA 10.0 grams omega-3 polyunsaturated fatty acids from fish oil These components were obtained in liquid form from a commercial source known as Impact®, (Sandoz Nutrition; Minneapolis, Min.) which was lyophilized to a powder and pelleted with 1.0% methyl cellulose. The standard diet which served as the control consisted of a commercially available pelleted rodent chow Teklad® (Harlan Industries, Indianapolis, Ind).

The donor specific transfusion procedure consisted of anesthetizing male ACI rats with 60 mg/Kg pentobarbital that was injected interperitoneally (i.p). Their blood was then anticoagulated systemically by injecting 100 units of heparin via the dorsal penile vein. Whole blood was collected by direct cardiac puncture and 1.0 ml. was transfused immediately into an anesthetized male Lewis rat recipient via the penile vein.

Cyclosporine (Sandoz Pharmaceuticals, East Hanover, N.J.) was obtained in a liquid concentrate and diluted with natural olive oil to a concentration of 5.0 mg/ml.

Heterotopic abdominal cardiac transplantation was performed using a modification of the method of Ono and Linsey (Improved Technique of Heart Transplantation in Rats, J. Thoracic Cardio. Surg. 55 1107–1112 (1969). Both donor and recipient animals were anesthetized with 60 mg./kg. pentobarbital prior to operation. Rejection of the grafts were determined by the loss of a palpable heartbeat and confirmed by laparotomy, the date of the transplantation being considered day 0. Grafts from animals that were rejected or found dead were stored in buffered formalin and were subjected to histologic confirmation of rejection if needed. Technical failure, defined as death or graft loss within 72 hours of operation were excluded from the analysis as well as any animals whose time of rejection was indeterminate.

Donor Specific transfusion (1.0 ml) was administered to some experimental recipients via the dorsal penile vein on the day prior to heart transplantation (D-1). Cyclosporine A was administered at a loading dose of 10.0 mg/kg subcutaneously (s.c.) on D-1 followed by 2.5 mg/kg/s.c. through the thirteenth day after transplantation (D+13). The immunomodulatory diet fortified with arginine, RNA and fish oil with omega-3-polyunsaturated fatty acids was substituted for standard laboratory rat chow beginning on D-1 and this was continued until death or rejection.

The recipients were divided up into six (6) different groups according to the diet and therapy received as follows:

Group 1—Control: rats given standard rat chow with no immunosuppression

Group 2—rats given immunomodulatory diet with no immunosuppression

Group 3—rats given immunomodulatory diet with cyclosporine alone.

Group 4—rats given standard rat chow with cyclosporine alone.

Group 5—rats given standard rat chow with cyclosporine and donor specific transfusion (immunosuppression).

Group 6—rats given immunomodulatory diet, cyclosporine and donor specific transfusion (immunosuppression).

Table 1 below discloses the survival rate for the respective groups in terms of the number of days of survival after cardiac allografts were implanted. The number of rats in each group is shown by the number of survival day numerals in the column. All results are also expressed as the mean ± standard error of the mean (SEM) and statistical significance was determined by the Kruskal-Wallis test.

TABLE 1

Survival of Cardiac Allografts in Treatment Groups

| Group | Survival (Days) | Means ± SEM | Significance ≦.05 |
|---|---|---|---|
| 1. Group 1 | 7,7,7,7,7,7,7,7 | 7.0 ± 0.0 | vs groups 2,3,4,5,6 |
| 2. Group 2 | 7,7,7,8,9,17,19,22 | 12.8 ± 2.1 | vs. groups 1,2 |
| 3. Group 3 | 9,18,18,20,32,40, 44,45,47 | 30.3 ± 4.8 | vs. groups 1, 2,5,6 NS vs 4 |
| 4. Group 4 | 15,18,18,19,25, 52,115 | 33.0 ± 9.5 | vs groups 1,2, 5,6 NS vs 3 |
| 5. Group 5 | 47,61,66,69,71, 92, 99 | 72.1 ± 6.8 | vs groups 1,2, 3,4,6 |
| 6. Group 6 | 40,84,179(D),335(SCC), 395(SCC), 389*, 389* 389* | 275 ± 53 | vs groups 1,2, 3,4,5 |

*= Living animal
(D)= Animals died with beating heart secondary to unrelated procedure under anesthesia.
(SCC)= Animals sacrificed with beating heart.

The above results clearly indicate a surprising and unexpected synergy between an complete enteral immunomodulatory diet and an immunosuppressive treatment for the treatment of allografts. Whereas the enteral diet by itself (Group 2) exhibits some potent immunomodulatory properties, the addition of the immunosuppressive treatment clearly maximizes the diet potential. Whereas the actual mechanisms behind this synergy are unknown, further refinement of the diet and/or therapy may ultimately provide a means to generate consistent donor specific tolerance without the risks of permanent systemic immunosuppression.

What I claim is:

1. An improved immunomodulatory therapy comprising the synergistic combination of an immunomodulatory diet and an immunosuppressive treatment for the enhancement of allograft survival and improved host defense mechanism, wherein said immunomodulatory diet comprises, administered in a daily dosage, a) from about 3.0 to about 40.0 grams of arginine, ornithine, or their salts or mixtures thereof;

b) from about 0.1 to about 4.0 grams of RNA or an mixtures thereof, and c) from about 0.1 to about 20.0 grams of omega-3 polyunsaturated fatty acids, and wherein said immunosuppressive treatment comprises the administration of donor specific transfusion and cyclosporine.

2. The immunomodulatory therapy of claim 1 wherein said immunomodulatory diet further comprises the daily adult requirement of vitamins, minerals, nitrogen, fatty acids and carbohydrates.

3. The improved immunomodulatory therapy of claim 2 wherein said donor specific transfusion comprises the administration of from about 100 to about 500 mls of anticoagulated whole blood from an appropriate blood donor.

4. The improved immunomodulatory therapy of claim 3 wherein said blood is anticoagulated and fractionated through cell separation prior to administration.

5. The improved immunomodulatory therapy of claim 4 wherein said cyclosporine is administered in a therapeutic amount of from about 5.0 mg/kg to about 15.0 mg/kg.

6. The improved immunomodulatory therapy of claim 5 wherein said immunomodulatory diet comprises:
   a) from about 10.0 to about 30.0 grams of arginine, ornithine, their salts and mixtures thereof;
   b) from about 1.0 to about 3.0 grams of RNA or an equivalent amount of nucleobase, nucleoside, nucleotide, DNA or mixtures thereof, and
   c) from about 0.10 to about 15.0 grams of omega-3-polyunsaturated fatty acids.

7. The improved immunomodulatory therapy of claim 6 wherein said immunomodulatory diet comprises the daily administration of:
   a) 15 to 22.0 grams of arginine, ornithine, their salts or mixtures thereof;
   b) 1.25 to 2.5 grams of RNA or an equivalent amount of nucleobase, nucleoside, nucleotide DNA or mixtures thereof, and
   c) 0.15 to 10.0 grams of omega-3-polyunsaturated fatty acids.

8. The immunomodulatory therapy of claim 7 wherein said diet comprises from 1.0 to 30.0 grams of medium chain fatty acids.

9. The immunomodulatory therapy of claim 7 in parenteral or enteral administration form that provides in one unit dose an energy supply of from 750 to 3500 kcal/day.

10. The immunomodulatory therapy of claim 8 providing an energy supply of from 1000 to 2000 kcal/day.

11. The immunomodulatory therapy of claim 9 which comprises a carbohydrate source providing for 40 to 70%, a nitrogen source providing for 15 to 30% and a fatty acid source providing for 15 to 30% of the total energy supply of the composition.

12. The immunomodulatory therapy of claim 11 wherein said omega-3-polyunsaturated fatty acids are selected from the group consisting of eicosapentaenoic acid and docosahexaenoic acid.

13. The immunomodulatory therapy of claim 12 wherein said omega-3-polyunsaturated fatty acids are from sources selected from the group consisting of linseed oil and fish oil.

14. The immunomodulatory therapy of claim 13 wherein said fish oil is selected from the group consisting of menhaden oil, salmon oil, mackerel oil, tuna oil and anchovy oil.

15. A method for improving survival after transplantation in a subject in need thereof comprising administering to said subject an immunomodulatory diet together with an immunosuppressive treatment consisting of the combination of donor specific transfusion and cyclosporine,
   wherein said immunomodulatory diet comprises, administered in a daily dosage,
   a) from about 3.0 to about 40.0 grams of arginine, ornithine, or their salts or mixtures thereof;
   b) from about 0.10 to about 4.0 grams of RNA or an equivalent amount of nucleobase, nucleoside, nucleotide, DNA or mixtures thereof; and
   c) from about 0.1 to about 20.0 grams of omega-3 polyunsaturated fatty acids.

16. The method of claim 15 wherein said immunomodulatory diet further comprises the daily adult requirement of vitamins, minerals, nitrogen, fatty acids and carbohydrates.

17. The method of claim 16 wherein said donor specific transfusion comprises the administration of from about 100 to about 500 ml of anticoagulated whole blood from an appropriate blood donor.

18. The method of claim 17 wherein said cyclosporine is administered in a concentration of from about 3.0 mg/kg to about 15 mg/kg.

* * * * *

UNITED STATES PATENT AND TRADEMARK OFFICE
CERTIFICATE OF CORRECTION

PATENT NO. : 5,612,060
DATED : March 18, 1997
INVENTOR(S) : J. Wesley Alexander

It is certified that error appears in the above-identified patent and that said Letters Patent is hereby corrected as shown below:

Column 1, line 5, should read

---- The US Government has a paid-up license in this invention and the right in limited circumstances to require the patent owner to license others on reasonable terms as provided for by the terms of Grant No. AI-12936, awarded by the National Institute of Health. ----

Signed and Sealed this

Thirty-first Day of March, 1998

*Attest:*

BRUCE LEHMAN

*Attesting Officer*   *Commissioner of Patents and Trademarks*